(12) United States Patent
Barthelmes et al.

(10) Patent No.: US 12,076,742 B2
(45) Date of Patent: Sep. 3, 2024

(54) ELECTROSTATIC ATOMIZER FOR LIQUIDS

(71) Applicant: J. Wagner GmbH, Markdorf (DE)

(72) Inventors: Jan Barthelmes, Salem (DE); Alfred Göhring, Salem (DE); Thomas Jeltsch, Friedrichshafen (DE); Holger Stohl, Markdorf (DE); Urban Bischofberger, Berneck (CH)

(73) Assignee: J. Wagner GmbH, Markdorf (DE)

( * ) Notice: Subject to any disclaimer, the term of this patent is extended or adjusted under 35 U.S.C. 154(b) by 130 days.

(21) Appl. No.: 16/657,142

(22) Filed: Oct. 18, 2019

(65) Prior Publication Data

US 2020/0114377 A1    Apr. 16, 2020

Related U.S. Application Data

(63) Continuation of application No. PCT/EP2018/060120, filed on Apr. 19, 2018.

(30) Foreign Application Priority Data

Apr. 21, 2017   (DE) .................... 10 2017 108 613.7

(51) Int. Cl.
*B05B 5/043* (2006.01)
*B05B 5/053* (2006.01)
(Continued)

(52) U.S. Cl.
CPC .............. *B05B 5/043* (2013.01); *B05B 5/053* (2013.01); *B05B 5/1691* (2013.01);
(Continued)

(58) Field of Classification Search
CPC ....... B05B 5/043; B05B 5/053; B05B 5/1691; B05B 12/002; B05B 12/081; B05B 12/12;
(Continued)

(56) References Cited

U.S. PATENT DOCUMENTS

| 4,467,961 A * | 8/1984 | Coffee ................ A01M 7/0089 239/1 |
| 2005/0212879 A1 | 9/2005 | Chiao et al. |

(Continued)

FOREIGN PATENT DOCUMENTS

| CN | 204656234 U | 9/2015 |
| CN | 204971225 U | 1/2016 |

(Continued)

OTHER PUBLICATIONS

English translation of International Preliminary Report on Patentability (Chapter I) (Application No. PCT/EP2018/060120) dated Oct. 31, 2019, 9 pages.

(Continued)

*Primary Examiner* — Cody J Lieuwen
(74) *Attorney, Agent, or Firm* — BURR PATENT LAW, PLLC

(57) ABSTRACT

An electrostatic atomizer for liquids, in particular cosmetics, is proposed, at least comprising a housing, an electrical energy source, an activation mechanism, control electronics, a high-voltage source, a liquid tank, a delivery device and atomizer nozzles, the control electronics and the high-voltage source being arranged in an interior space of the housing. It is provided that the control electronics either comprise at least one sensor or comprise at least one transmitting and/or receiving module or comprise at least one sensor and at least one transmitting and/or receiving module.

13 Claims, 1 Drawing Sheet

(51) Int. Cl.
  *B05B 5/16* (2006.01)
  *B05B 12/00* (2018.01)
  *B05B 12/08* (2006.01)
  *B05B 12/12* (2006.01)
  *A61M 35/00* (2006.01)

(52) U.S. Cl.
  CPC ............ *B05B 12/081* (2013.01); *B05B 12/12* (2013.01); *A45D 2200/057* (2013.01); *A61M 35/25* (2019.05); *B05B 12/002* (2013.01)

(58) Field of Classification Search
  CPC ............ A45D 34/02; A45D 2200/057; A61M 35/003; A61M 35/25; A61M 35/30
  See application file for complete search history.

(56) References Cited

U.S. PATENT DOCUMENTS

| | | | |
|---|---|---|---|
| 2009/0200392 A1 | 8/2009 | Duru et al. | |
| 2010/0116897 A1 | 5/2010 | Lind et al. | |
| 2013/0002854 A1* | 1/2013 | Nielsen | B65D 83/203 348/94 |
| 2013/0146684 A1* | 6/2013 | Minakuchi | B05B 5/00 239/690 |
| 2014/0079652 A1* | 3/2014 | Cooper | B05B 16/00 424/59 |
| 2014/0151471 A1 | 6/2014 | Dau et al. | |
| 2015/0297776 A1* | 10/2015 | Conroy | B05B 12/08 239/11 |
| 2016/0022009 A1 | 1/2016 | Rabe et al. | |
| 2016/0022011 A1* | 1/2016 | Rabe | A61B 5/4839 132/200 |
| 2017/0087576 A1 | 3/2017 | Fang et al. | |
| 2017/0151577 A1* | 6/2017 | Baltz | B05B 5/005 |

FOREIGN PATENT DOCUMENTS

| | | |
|---|---|---|
| EP | 2 025 411 A1 | 2/2009 |
| JP | 2012-105956 A1 | 6/2012 |
| JP | 2013-094719 A | 5/2013 |
| KR | 10-2013-0059430 A | 6/2013 |
| KR | 10-2014-0046020 A | 4/2014 |
| KR | 10-2017-0023137 A | 3/2017 |
| WO | 2016/014886 A1 | 1/2016 |
| WO | 2016/057942 A2 | 4/2016 |

OTHER PUBLICATIONS

European Office Action (Application No. 18 719 152.3) dated Oct. 8, 2020.
Chinese Office Action (Application No. 201880040551.7) dated Dec. 30, 2020 (English translation only).
International Search Report and Written Opinion (Application No. PCT/JP2018/060120) dated Jun. 14, 2018.
Japanese Office Action (Application No. 2019-557479) dated Jan. 11, 2022 (with English translation).
Korean Office Action (with English translation) dated Jun. 17, 2022 (Application No. 10-2019-7034212).

* cited by examiner

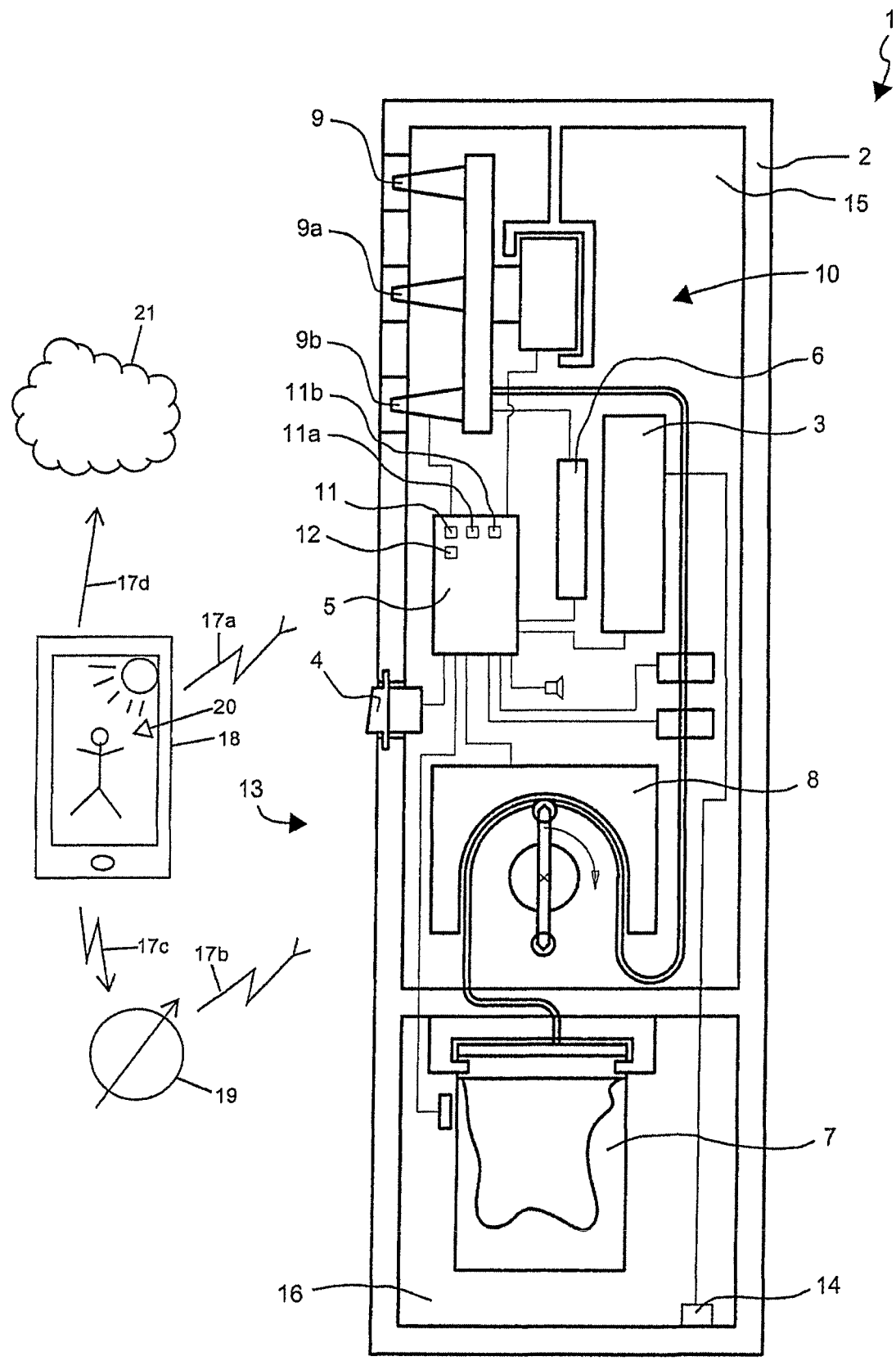

ELECTROSTATIC ATOMIZER FOR LIQUIDS

CROSS REFERENCE TO RELATED APPLICATIONS

This application is a continuation of International Application No. PCT/EP2018/060120 filed Apr. 19, 2018, which designated the United States, and claims the benefit under 35 USC § 119(a)-(d) of German Application No. 10 2017 108 613.7 filed Apr. 21, 2017, the entireties of which are incorporated herein by reference.

FIELD OF THE INVENTION

The present invention relates to an electrostatic atomizer for liquids.

BACKGROUND OF THE INVENTION

Electrostatic atomizers for liquids are already known from the prior art, for example, from US 2010/0116897 A1. The known atomizer has the disadvantage that individual needs of a user, in particular, based on user data, cannot be taken into account during the operation of the atomizer.

SUMMARY OF THE INVENTION

The object of the present invention is to provide an electrostatic atomizer for liquids that can be operated very reliably and flexibly or adaptively while taking into account individual needs of the user.

In the context of the present invention, electrostatic atomization comprises all atomization processes that atomize liquids with effects under the influence of a high voltage. In particular, electrohydrodynamic effects and electrokinetic effects are also covered by the concept of this type of atomization. In the context of the present invention, an electrostatic atomization may also be understood as meaning an electrohydrodynamic atomization.

Proposed is an electrostatic atomizer for liquids, in particular, cosmetics, which comprises at least one housing, an electrical energy source, an activation mechanism, control electronics, a high-voltage source, a liquid tank, a delivery device and also atomizer nozzles, the control electronics and the high-voltage source being arranged in an interior space of the housing.

More broadly, the activation mechanism may be formed as a button, but also as a capacitive switch, as a dry-reed contact or as a Hall sensor. In addition or alternatively, an activation mechanism may be provided in the form of a main switch, for example, a housing slide, or a function may be enabled by way of a device connected via a transmitting and receiving unit, for example, a smartphone.

According to the present invention, it is provided that the control electronics either comprise at least one sensor or comprise at least one transmitting and/or receiving module or comprise at least one sensor and at least one transmitting and/or receiving module. The use of a sensor or a transmitting and/or receiving module allows user-specific data to be taken into account during the operation of the atomizer. In this way, allowance can be made for individual needs of a user during the operation or use of the atomizer.

The term sensor should in this case be understood in a broad sense. In principle, sensors are also to be regarded as devices for detecting physical parameters, such as, for example, current flow, voltage, temperature, light intensity, etc. Sensors may, however, also be movement sensors in the form of gyro sensors, or position and acceleration may be detected. Optical sensors, such as, for example, brightness sensors or the like, are also included.

The transmitting-receiving module serves for communication with external devices. Whether standards such as wireless LAN, Bluetooth or Mobile Internet (for example, LTE) are used for the communication depends on the respective particular use.

Moreover, an atomizer according to the present invention can be operated reliably and individually, since a sensor or a transmitting and/or receiving module can provide data on operation or else during operation and, in particular, when there are changes of data, make corresponding allowances or adapt the operation of the atomizer correspondingly. Consequently, the atomizer also has a high degree of flexibility or adaptability with regard to its use.

The atomizer according to the present invention may be intended for many types of operation. In this respect, a sunscreen, for example, may be used in a similar way to the application of insect repellent or a deodorant. Industrial uses with paints or lacquers would also be conceivable.

A preferred refinement of the present invention may provide that the at least one sensor is formed for detecting the voltage and/or the current intensity of the high-voltage source, in particular, the loading of the high-voltage source. In this way, for example, the output of the delivery device can be influenced and/or evaluated, whereby the spraying result can be influenced.

In order to be able to influence the output of the delivery device, and, in particular, regulate the amount of liquid dispensed from the atomizer nozzles, it may be provided in an advantageous refinement of the present invention that the at least one sensor is formed for detecting the intensity and/or the wavelength of incident light.

In the example of use for applying sunscreen fluids, a UV sensor would make it possible to calculate when the sunscreen should be reapplied. In this case, not only can ambient data such as the intensity of the sunlight and the temperature be included, but also individual profiles for the respective user can be defined, taking into consideration a relevant skin type or how the skin has previously been affected, for example, by sunburn.

For further influencing or controllability of the output of the delivery device, in particular, also with regard to an amount of liquid to be dispensed from the atomizer nozzles or the temperature of liquid emerging, the present invention may provide that the at least one sensor is formed for detecting the temperature and/or the humidity of the air in the surrounding area of the atomizer.

In order to make it possible for the atomizer to be operated while taking into account user-specific data, in an advantageous development of the present invention it may be provided that the at least one transmitting and/or receiving module can be connected via a radio link to a cell phone or tablet or similar computer.

In this way, a personalization of the operating mode of the atomizer can take place. For example, in the case where sunscreen is used, the specific skin type may be determined, measured or stored by external data in the smartphone. Then, the application of the sunscreen by the atomizer can be performed exactly appropriately for the skin type, while additional environmental influences, such as, for example, temperature and air humidity, can also be taken into account if they influence the application result.

In order to be able to use the atomizer, for example, also as a freely transportable device, consequently to make more flexible use of the atomizer in different locations possible, the present invention may also provide in a refinement that the energy source is formed as a chargeable electrical store (storage battery) and the atomizer comprises at least one charging device for charging the energy source, the charging device being formed, in particular, as a standardized connection, preferably as a USB connection. Chargeable energy sources also have a long service life. Standardized connections are obtainable at low cost and corresponding charging technology is readily available.

A further advantageous development of the present invention may provide that the energy source is formed as a chargeable electrical store (storage battery) and the atomizer comprises at least one charging device for charging the energy source, while the charging device is formed as an electromagnetic coil of an inductive charging device, the coil preferably being arranged within the housing, either on a head portion or on a grip portion. Such a charging possibility by means of induction has the advantage that the atomizer can, for example, be removed from a charging station without plugging in or removing an electrical line, for example, a cable, after before or after the charging. Moreover, by remaining free of appropriately arranged openings for the connection of charging lines, etc., penetration of moisture or dirt, etc., into such openings can be prevented. As a result, the service life of the atomizer can be increased.

In order to achieve a spraying result that corresponds to individual needs of a user, a further advantageous development of the present invention may provide that the at least one sensor is formed for detecting an amount of liquid taken from the liquid tank or for detecting a filling level of liquid in the liquid tank.

A corresponding sensor system allows the coating amount, and consequently possibly indirectly the layer thickness, of the fluid applied by the atomizer to be determined, or at least estimated, so that conclusions can be reached concerning the success of coating. In this case, advantageously a detection of the movement of the atomizer and/or of the distance from the coated surface would possibly also have to be considered.

The atomizer according to the present invention can be used even more flexibly with regard to taking individual needs into account if the control electronics comprise a number of sensors for detecting the temperature and/or humidity of the air in the surrounding area of the atomizer and for detecting the intensity and/or the wavelength of incident light and for detecting the voltage and/or the current intensity.

By intelligently taking into account the data of a number of sensors, for example, of the amount dispensed, movement patterns, the distance from the surface and also the exposure to sun rays, optimized and personalized scenarios of use, in terms of amount and frequency, can be achieved, for example, in the case of sunscreen application. Any desired combinations of sensor data and control instructions for other particular uses are also conceivable.

One embodiment of the atomizer according to the present invention provides that a memory, in particular, an RFID marking on the liquid tank, can be read and/or written by the control electronics. The memory on the one hand allows the liquid tank to be identified and on the other hand, if the memory can also be flexibly written, provides the possibility of storing, updating or making readable for other devices use-specific data, such as, for example, the day of first opening or a residual filling amount. In this way, liquid tanks can be designed as sustainably exchangeable. Changing between different atomizer devices is also thereby made possible.

In an embodiment of the atomizer in which the control electronics comprise one or more sensor for detecting a position and/or a movement in space, with the control electronics making it possible for changes in position and/or movement sequences to be detected, stored and analyzed, use data of the individual user can be detected and evaluated. In particular, in interaction with an external device, for example, a smartphone, a movement pattern can allow a conclusion to be reached concerning the sprayed locations or areas.

According to the present invention, a method for operating an atomizer described above is also provided. In the case of the method, it is provided that the control electronics transfer sensor data from at least one sensor via at least one transmitting and/or receiving module to an external device and the external device processes the data and/or displays them and/or passes them on.

By this method, it is, for example, possible to indicate filling levels of the liquid tank on a smartphone, to transmit and personalize the set device parameters or to process detected movement data. The use, in particular, the frequency and intensity of the use, of the atomizer can also be transferred, and, for example, passed on to a cloud or a database.

In the case of a further embodiment of the method, it is provided that the control electronics obtain sensor data of at least one sensor via at least one transmitting and/or receiving module from an external device, and the control electronics process and/or display and/or pass on these data. Sensor data of an external device, for example, a temperature sensor or the like, can likewise be transferred to the atomizer, so that the latter can use these data and adapt the operating state accordingly. If the atomizer is, for example, operated at a location that requires a considerable frequency of use in the case of the use of a sunscreen (great exposure to sun), the position can be determined by the GPS sensor of the smartphone, and the typical data for this region can be used to perform on the atomizer a control of the amount of liquid dispensed.

In a comparable way, the method may also be used for operating an atomizer to the extent that the control electronics transfer data concerning operating states and/or device parameters via at least one transmitting and/or receiving module to an external device and the external device processes and/or displays and/or passes on the data.

A smartphone may log and evaluate the frequency of use and the amount taken from the liquid tank. If there is insufficient use, it is possible, for example, by an app on the external device, for example, the smartphone, to signal that renewed use is recommended.

In a corresponding way, in the case of the method for operating an atomizer, it may also be provided that the control electronics obtain data via at least one transmitting and/or receiving module from an external device and the control electronics process and/or display and/or pass on these data, in particular, use them for providing operating states or device parameters.

The use of data of the external device, for example, the smartphone, for example, concerning detected successes of coating or analyses of the needs of the user, can also be reported back to the atomizer, so that the latter automatically adapts its operating states or parameters.

BRIEF DESCRIPTION OF THE DRAWING

The present invention is explained in more detail below on the basis of a drawing, from which further features that are essential to the present invention and advantages of the present invention emerge.

FIG. 1 shows an atomizer according to the present invention in a greatly simplified schematic representation.

DETAILED DESCRIPTION OF THE INVENTION

The electrostatic atomizer 1 comprises a housing 2 with an interior space 10, in which housing 2 an electrical energy source 3, an activation mechanism 4, control electronics 5, a high-voltage source 6, a liquid tank 7, a delivery device 8 and atomizer nozzles 9, 9a, 9b are arranged.

In the exemplary embodiment shown, the control electronics 5 comprise sensors 11, 11a, 11b and a transmitting and/or receiving module 12.

Sensors 11, 11a, 11b may be intended or designed to allow the voltage and/or the current intensity and/or the wavelength of incident light or the temperature and/or the humidity of the air in the surrounding area 13 of the atomizer 1 to be detected. In this way, correspondingly determined data can, for example, influence a delivery output of the delivery device 8, and consequently also a spraying result of the atomizer 1.

Sensors 11, 11a, 11b may also be intended or designed to determine or to detect distances between atomizer nozzles 9, 9a, 9b and an object to be sprayed (not shown) by field analysis.

Sensors 11, 11a, 11b may also be intended or designed to allow an area of a sprayed object to be determined or detected.

Furthermore, sensors 11, 11a, 11b may be intended or designed to allow optical analyses of an object to be sprayed to be carried out.

Sensors 11, 11a, 11b may also be provided or appropriately designed to allow repeated uses, for example, multiple uses, to be detected and/or for them to be prevented.

Sensors 11, 11a, 11b may also be intended or designed to allow an alignment of the atomizer nozzles 9, 9a, 9b with regard to an object to be sprayed to be determined, for example by comparison of the respective potentials of the atomizer nozzles 9, 9a, 9b.

The transmitting and/or receiving module 12 may, for example, be intended to be connected via a radio link to a cell phone or tablet (not represented). It may also be provided, for example, that data of a user, for example, bodyweight, body size, are transferred from a cell phone or tablet to the atomizer 1, and correspondingly adapted spraying operations are carried out. Such spraying operations may then be carried out individually, and, for example, also only concern individual parts of a user's body.

By means of corresponding monitoring of the spraying activity of the atomizer with regard to chosen requirements by sensor elements 11, 11a, 11b or the transmitting and/or receiving module 12, an established spraying result can possibly be corrected. In particular, the time and the sprayed amount of liquid may be monitored here, and possibly further spraying operations carried out. A monitoring or checking of spraying operations may also be performed on the basis of image data, which are, for example, transmitted from a smartphone or tablet to the atomizer 1.

In the exemplary embodiment shown, the atomizer 1 comprises an electrical energy source 3, which is chargeable. For this purpose, the atomizer 1 comprises a charging device 14, which is arranged in a grip region 16 of the atomizer within or in an interior space 10 of the housing 2.

The transmitting/receiving module 12 can be used to establish a connection via a radio link 17a, for example, WLAN or Bluetooth, to an external device, for example, a smartphone 18, or via a radio link 17b to an external sensor 19. A simultaneous connection to a number of devices, in particular, sensors 19, is also conceivable.

The data of the internal sensors 11a and 11b and/or of the external sensors 19 and/or of the smartphone 18 may then be processed in the smartphone 18 in an app 20 and instructions and recommendations for the user may be output, for example, on the screen. A remote control of the atomizer 1 from the smartphone 18 is also conceivable.

There is furthermore the possibility that the smartphone 18 is also connected directly via a radio link 17c to a sensor, and the data of the latter are evaluated and for example UV values are passed on to the app 20, and consequently to the atomizer 1.

What is more, it is provided that data are transferred via a radio link 17d to an external computing center, for example, a cloud 21, in order to store user profiles or perform statistical evaluations.

In the context of the present invention, an electrostatic atomization may also be understood as meaning an electrohydrodynamic atomization.

In the context of the present invention, a liquid should be understood as meaning any kind of liquid. In the context of the present invention, the liquid may be a cosmetic, also liquid paint or lacquer or the like.

LIST OF DESIGNATIONS

1 Atomizer
2 Housing
3 Electrical energy source
4 Activation mechanism (button or switch)
5 Control electronics
6 High-voltage source
7 Liquid tank
8 Delivery device
9 Atomizer nozzle
9a Atomizer nozzle
9b Atomizer nozzle
10 Interior space
11 Sensor
11a Sensor
11b Sensor
12 Transmitting and/or receiving module
13 Surrounding area (of the atomizer)
14 Charging device
15 Head portion
16 Grip portion
17a Radio link smartphone—atomizer
17b Radio link sensor—atomizer
17c Radio link smartphone—sensor
17d Radiolink smartphone—cloud
18 Smartphone
19 Sensor
20 App
21 Cloud/Internet

The invention claimed is:

1. A handheld electrostatic cosmetic atomizer, comprising:
a housing having a grip portion and having an interior space in which an electrical energy source, an activation mechanism, control electronics, a voltage source, and atomizer nozzles are arranged;

a liquid tank containing a cosmetic liquid; and a memory in the form of an RFID marking on the liquid tank, which is read by and written to the control electronics, wherein the memory is situated on the liquid tank and is physically separate from, but immediately adjacent to the control electronics located within the housing, and wherein the memory is located proximate and below the atomizer nozzles in a use state of the handheld atomizer, wherein the control electronics comprise at least one first sensor that detects an amount of the cosmetic liquid taken from the liquid tank, wherein the control electronics comprise second sensors and at least one transmitting and/or receiving module, wherein the second sensors of the control electronics each detect a movement of the atomizer in space, whereby the control electronics detect, store and analyze changes in movement sequences of the handheld atomizer, wherein the control electronics detect and store use data of the handheld wherein the at least one transmitting and/or receiving module provides user specific data about an individual user to the atomizer, and atomizer from the individual user and the user specific data about the individual user, so that the handheld atomizer dispenses the cosmetic liquid based on the use data of the handheld atomizer for the individual and the user specific data about the individual user.

2. The handheld electrostatic cosmetic atomizer as claimed in claim 1, wherein the control electronics further comprise at least one sensor that detects an intensity and/or a wavelength of incident light.

3. The handheld electrostatic cosmetic atomizer as claimed in claim 1, wherein the control electronics further comprise at least one sensor that detects an air temperature and/or a humidity of air in an area surrounding the atomizer.

4. The handheld electrostatic cosmetic atomizer as claimed in claim 1, wherein the electrical energy source is a chargeable electrical store, and wherein the handheld atomizer further comprises at least one charging device for charging the electrical energy source, wherein the charging device has a standardized connection.

5. The handheld electrostatic cosmetic atomizer as claimed in claim 4, wherein the electrical energy source is a chargeable electrical store, wherein the handheld atomizer further comprises at least one charging device for charging the electrical energy source, wherein the charging device is an electromagnetic coil of an inductive charging device, and wherein the electromagnetic coil is arranged within the housing, either on a head portion or on the grip portion.

6. The handheld electrostatic cosmetic atomizer as claim in claim 4, wherein the charging device has a USB connection.

7. The handheld electrostatic cosmetic atomizer as claimed in claim 1, wherein the control electronics comprise a number of sensors that detect a temperature and/or a humidity of air in an area surrounding the handheld atomizer, and that detect an intensity and/or a wavelength of incident light.

8. A method for operating the handheld electrostatic cosmetic atomizer as claimed in claim 1, wherein the control electronics transfer sensor data from at least one of the at least one sensor via at least one of the at least one transmitting and/or receiving module to an external device, and wherein the external device performs at least one of processing the data, displaying the data, and transmitting the data.

9. A method for operating the handheld electrostatic cosmetic atomizer as claimed in claim 1, wherein the control electronics obtain sensor data of at least one of the first and second sensors via at least one of at least one transmitting and/or receiving module from an external device, and wherein the control electronics performs at least one of processing the data, displaying the data, and transmitting the data.

10. A method for operating the handheld electrostatic cosmetic atomizer as claimed in claim 1, wherein the control electronics transfer data concerning operating state data and/or device parameter data via at least one of the at least one transmitting and/or receiving module to an external device, and wherein the external device performs at least one of processing the data, displaying the data, and transmitting the data.

11. A method for operating the handheld electrostatic cosmetic atomizer as claimed in claim 1, wherein the control electronics obtain data via at least one of the at least one transmitting and/or receiving module from an external device, and the control electronics process and/or display transmit the data to provide operating states or device parameters.

12. The handheld electrostatic cosmetic atomizer according to claim 1, wherein the control electronics further comprise at least one sensor that detects a voltage and/or a current intensity of the voltage source.

13. The handheld electrostatic cosmetic atomizer according to claim 1, wherein the at least one transmitting and/or receiving module is connectable via a radio link to a cell phone or tablet.

* * * * *